United States Patent
Shah et al.

(10) Patent No.: US 6,387,450 B1
(45) Date of Patent: May 14, 2002

(54) METHOD FOR PREPARING A BIOCOMPATIBLE COATING

(75) Inventors: Chirag B. Shah, Nashua, NH (US); John A. Hudson, Wells, ME (US); Eugene Tedeschi, Still River, MA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/708,472

(22) Filed: Nov. 9, 2000

Related U.S. Application Data

(62) Division of application No. 09/163,240, filed on Sep. 30, 1998, now Pat. No. 6,160,032.

(51) Int. Cl.$^7$ ................................................ B05D 3/02
(52) U.S. Cl. .................... 427/385.5; 427/2.24; 623/926
(58) Field of Search .............................. 427/385.5, 2.24; 623/926

(56) References Cited

U.S. PATENT DOCUMENTS

| | | | |
|---|---|---|---|
| 4,487,865 A | 12/1984 | Balazs et al. | 524/29 |
| 4,500,676 A | 2/1985 | Balazs et al. | 525/54.2 |
| 4,585,666 A | 4/1986 | Lambert | 427/2 |
| 4,663,233 A | 5/1987 | Beavers | 428/412 |
| 4,801,475 A | 1/1989 | Halpern et al. | 427/338 |
| 5,023,114 A | 6/1991 | Halpern et al. | 427/338 |
| 5,037,677 A | 8/1991 | Halpern et al. | 427/338 |
| 5,116,374 A | * 5/1992 | Stone | 623/16 |
| 5,356,433 A | 10/1994 | Rowland et al. | 623/11 |
| 5,607,475 A | 3/1997 | Cahalan et al. | 623/11 |

FOREIGN PATENT DOCUMENTS

| WO | WO-99/43728 | * 9/1999 |
|---|---|---|

OTHER PUBLICATIONS

Magnani et al, J. Mater. Chem., 9(10), pp. 2393–2398, 1999.*

* cited by examiner

Primary Examiner—Erma Cameron
(74) Attorney, Agent, or Firm—Sterne, Kessler, Goldstein & Fox P.L.L.C.

(57) ABSTRACT

A coating composition is provided comprising hyaluronic acid or a salt thereof and a blocked polyisocyanate in a solvent comprising water. A method is provided for preparing the coating on a substrate comprising forming a coating mixture of hyaluronic acid or a salt thereof and a blocked polyisocyanate in a solvent comprising water; applying the coating mixture to the substrate; and curing the coating.

4 Claims, No Drawings

METHOD FOR PREPARING A BIOCOMPATIBLE COATING

RELATED APPLICATION

The present application is a divisional application of U.S. Utility Patent Appl. No. 09/163,240, filed on Sep. 30, 1998, now U.S. Pat. No. 6,160,032.

FIELD OF THE INVENTION

This invention relates to a lubricious, biocompatible, biomimetic coating composition, which may be applied to a substrate in one step, comprising hyaluronic acid or a salt thereof, a blocked polyisocyanate, and a solvent, particularly water. The invention also relates to a method for producing the lubricious, biocompatible, biomimetic coating.

BACKGROUND OF THE INVENTION

It has long been known that hydrophilic coatings with low friction (coefficient of friction of 0.3 or less) are useful for a variety of medical devices such as catheters, catheter introducers and the like. When low friction surfaces are used, the devices, upon introduction into the body, slide easily within arteries, veins, cannula and other passageways and body orifices. There have been a wide variety of methods used to provide the surfaces desired. In some cases the material of the catheter or medical device is formed of a material having inherently good anti-friction properties, such as poly(tetrafluoroethylene) or other plastics. However, in many cases the selection of materials does not provide the properties desired in conjunction with other desirable properties for the particular medical device.

Prior art hydrophilic coatings typically rely on a two step, two coating process, usually involving a primer coat of isocyanate or isocyanate/polymer blend which is dried, followed by a second coat containing at least one hydrophilic polymer such as polyvinyl pyrrolidone or poly(ethylene oxide). The two coatings, one superimposed on the other, are then baked to effect a cure. This forms an interpolymer complex or a network including the hydrophilic polymer.

Prior patents have suggested applying solutions of polyvinylpyrrolidone with isocyanate and/or polyurethane in multi-step operations. These coatings often lack good durability. For example, U.S. Pat. No. 4,585,666 issued to Lambert discloses medical devices having hydrophilic coatings formed from an isocyanate layer overcoated with a polyvinylpyrrolidone layer. However, the multistep procedure makes it difficult to tailor the properties and values of the final coatings.

U.S. Pat. No. 5,356,433, Rowland et al., describes a two step method for preparing metal surfaces of medical devices with enhanced biocompatability properties. The method includes covalently linking an organosilane compound having amine reactive sites with the metallic surface of the medical device. A biologically active agent is covalently linked to the organosilane compound.

U.S. Pat. No. 5,607,475, Cahalan et al., discloses a two step method for preparing a metal or glass surface of a medical device with improved biocompatibility. The method includes applying to the surface of a medical device a silane compound having a pendant vinyl functionality such that the silane adheres to the surface. A graft polymer is then formed on the surface with vinylsilane such that the pendant vinyl functionality of the vinylsilane is incorporated into the graft polymer by covalent bonding with the polymer. Biomolecules are then covalently bonded to the graft polymer.

U.S. Pat. No. 5,037,677, Halpern et al., describes a two step method of interlaminar grafting of coatings upon an object, such as a plastic medical device, in order to bond sodium hyaluronate to the surface of the object. The method includes coating the object with an anchor coat containing an acrylic polymer having a grafting functionality in a solvent. The grafting functionality may be an isocyanate group. The object is then coated with an aqueous solution containing sodium hyaluronate. The coatings are heated and the grafting functionality in the anchor coat reacts with the sodium hyaluronate to form covalent bonds resulting in interlaminar grafting. The isocyanate groups, however, easily react with atmospheric moisture thereby becoming less available or unavailable for reaction with the sodium hyaluronate resulting in a poor coating.

There are several disadvantages to the two step process. First, the exact ratio of primer material to the hydrophilic polymer is difficult to control, as it depends on the amounts of primer and hydrophilic polymer which happen to be deposited by the wet film during the respective coating steps. Second, the primer may begin to redissolve in the second coating solution, causing some loss of primer and further resulting in difficulty in controlling the primer/hydrophilic polymer ratio. Third, since the hydrophilic polymer is not covalently bonded to the substrate, it may bond to other materials in the area, leading the coating to lose its desired properties. Fourth, additional facilities, time, and cost are needed for coating with a two step process, as is compared to a one step process.

The present invention provides a coating having hyaluronic acid which may be applied in a single step, alleviates the need for a primer or coupling agent, and can be applied on various substrates, including, but not limited to, metals and plastics.

Hyaluronic acid is a biopolymer which is present in the human body in body fluids, joints, and mucous membranes. The biological functions of hyaluronic acid include protection, lubrication and separation of cells, regulation of transport of molecules and cell metabolites, and maintenance of the structural integrity of connective tissues and fluid retention intercellular matrix.

SUMMARY OF THE INVENTION

The present invention provides a coating composition comprising hyaluronic acid or a salt thereof and a blocked polyisocyanate in a solvent comprising water.

According to another embodiment of the present invention, an article is provided comprising a substrate to which a coating composition comprising hyaluronic acid or a salt thereof and a blocked polyisocyanate in a solvent comprising water, is applied.

According to yet another embodiment of the invention, a method of preparing a coating on a substrate to be coated comprises forming a mixture of hyaluronic acid or a salt thereof and a blocked polyisocyanate in a solvent comprising water; applying the mixture to the substrate; and curing the mixture on the substrate to form the coating.

These and other features and objects of the invention are more fully appreciated from the following detailed description of a preferred embodiment of the invention.

DETAILED DESCRIPTION OF A PREFERRED EMBODIMENT

According to the present invention, a coating is formed from the reaction on a substrate to be coated of a mixture comprising hyaluronic acid or a salt thereof and a blocked polyisocyanate in a solvent. The solvent comprises water and, optionally, a water miscible cosolvent. The resulting coating is highly lubricious and thromboresistant.

The coating composition is prepared by weighing the appropriate quantities of hyaluronic acid or salt thereof, blocked polyisocyanate, and solvent into an appropriate mixing vessel. Additional solvents may be added to adjust the viscosity of the mixture. Solids contents in a range of from about 0.1 to about 25% and viscosities in the range of 50 cps to 500 cps are preferred. This solution is mixed well and then applied to an appropriate substrate, such as catheter tubes, medical tubing introducers, polymer coated medical wires, stents, guide wires, and dilatation balloons, by conventional coating application methods. Such methods include, but are not limited to, dipping, spraying, wiping, painting, and the like.

After applying the coating solution, the solvent is preferably allowed to evaporate from the coated substrate, such as by exposure to ambient conditions for at least 5 minutes.

The coating is subsequently cured. The cure time, temperature, and humidity vary with the choice of hyaluronic acid or salt thereof, blocked polyisocyanate, solvent, and the composition of the substrate. The ratio of ingredients in the coating mixture also affects the physical properties of the overall coating. The amount of sodium hyaluronate controls the lubricity of the coating. The amount of blocked polyisocyanate controls the flexibility of the coating.

Cure temperatures may range from about 120° C. to about 150° C. Cure times may range from about 5 minutes to about 1 hour, depending upon the cure temperature and the reactivity of the hyaluronic acid or salt thereof and blocked polyisocyanate. In all cases the cure conditions should be non-deleterious to the underlying substrate.

After the coating is cured, it is preferable to rinse or soak the coating in water to remove any uncomplexed polymers. Generally, a brief rinse of 10–15 seconds is sufficient, however, a longer rinse or soak is acceptable since the coating is cured and forms a stable gel when in contact with water. After rinsing, the coating may be dried either at ambient conditions, or at elevated temperatures.

After the coating is formed, the coating can imbibe water from an aqueous solution prior to introduction to the body to become lubricious. Alternatively, the coating can imbibe water from body fluids, even if not exposed to water prior to introduction into the body. The coating retains its lubricating properties upon rehydration even when dried and remoistened repeatedly. If the coating is to be used for items such as catheters, introducer tubes and the like, the materials selected should be compatible with and non-toxic to the body. Since hyaluronic acid is a biopolymer, it is biocompatible. The coating may be applied to various substrates, including, but not limited to, metals, ceramics, organic materials including plastics, and glass.

The coating may be applied to metal substrates such as the stainless steel used for guide wires and other devices, nitinol which is an alloy of nickel and titanium, and tantalum.

The organic substrates which may be coated with the coatings of this invention include, but are not limited to, polyether block amide, polyethylene terephthalate, polyetherurethane, polyesterurethane, other polyurethanes, natural rubber, rubber latex, synthetic rubbers, polyester-polyether copolymers, and polycarbonates. Some of these materials are available under various trademarks such as Pebax™ available from Atochem, Inc. of Glen Rock, N.J.; Mylar™ available from E.I. duPont deNemours and Co. of Wilmington, Del.; Texin™ 985A from Mobay Chemical Corporation of Pittsburgh, Pa.; Pellethane™ available from Dow Chemical of Midland, Mich.; and Lexan available from General Electric Company of Pittsfield, Mass.

The hyaluronic acid preferably has an average molecular weight of from about 70,000 to about 6 million daltons, more preferably from about 300,000 to 2 million daltons, and most preferably from about 500,000 to about 1 million daltons. Preferably, the amount of hyaluronic acid ranges from about 0.1 to about 5 percent, by weight, based upon 100% total weight of coating composition. More preferably, the amount of hyaluronic acid ranges from about 0.1 to about 2 percent, by weight, and most preferably from about 0.25 to about 1 percent, by weight. Below about 0.2 percent hyaluronic acid, the coating is not very lubricious. Above 1 percent hyaluronic acid, the coating is too lubricious for most applications. As the average molecular weight increases, the amount of hyaluronic acid may be decreased.

A preferred salt of hyaluronic acid is sodium hyaluronate. Other usable salts include potassium hyaluronate. Derivatives of hyaluronic acid, such as sulfated or acetylated hyaluronic acid may also be used.

Preferably, the blocked polyisocyanate is hexamethylene diisocyanate and is dissolved in N-methyl-2-pyrrolidone; the amount of blocked polyisocyanate ranges from about 0.1 to about 5 percent, by weight, based upon 100% total weight of coating composition. More preferably, the amount of blocked polyisocyanate ranges from about 0.1 to about 2 percent, by weight, and most preferably from about 0.5 to about 2 percent by weight. Blocked polyisocyanates are generally reaction products of isocyanates with certain active hydrogen compounds such that the addition product has only limited thermal stability. For example, blocked polyisocyanates may be prepared by reacting polyisocyanates with phenol, m-cresol, diethyl malonate, ethyl acetoacetate, or e-caprolactam.

The ratio by weight of hyaluronic acid to blocked polyisocyanate preferably ranges from about 0.5:1 to about 2:1.

The solvent employed should be non-reactive with the hyaluronic acid or blocked polyisocyanate and is a solvent for all the components. The solvent comprises water and optionally, a water miscible cosolvent. Suitable cosolvents include, but are not limited to tetrahydrofuran, acetone,) acetonitrile, and dimethylsulfoxide. Preferably, the cosolvent is tetrahydrofuran.

Wetting agents may be added to the coating solution to improve wettability to hydrophobic surfaces. Wetting agents include, but are not limited to, fluorinated alkyl esters, such as Fluorad™ FC-430 available from 3M Corp., and octylphenol ethylene oxide condensates, such as Triton™ X-100 available from Union Carbide. A preferred concentration of wetting agent in the coating solution is from about 0.01 to about 0.2% by weight based upon 100% solids in the coating solution.

Drugs may be added to the coating mixture; the result is a drug eluting coating.

Viscosity and flow control agents may be added to the coating mixture to adjust the viscosity and thixotropy of the mixture to a desired level. The viscosity is such that the coating can be formed on the substrate at the desired thickness. Viscosities of from about 50 cps to about 500 cps may be used although higher or lower viscosities may be useful in certain instances. Viscosity control agents include, but are not limited to, fumed silica, cellulose acetate butyrate, and ethyl acrylate/2-ethyl hexyl acrylate copolymer. Flow control agents are preferably present in amounts of from about 0.05 to about 5 percent, by weight, based upon 100% total weight of coating composition and more preferably in amounts of from about 0.1 to about 2 percent. Flow control agents include acrylic copolymers, including Modaflow™ available from Monsanto.

Antioxidants may be added to the coating mixture to improve oxidative stability of the cured coatings. Antioxidants include, but are not limited to, tris(3,5-di-t-butyl-4-hydroxy benzyl) isocyanurate, 2,2'-methylenebis(4-methyl-6-t-butyl phenol), 1,3,5-trimethyl-2,4,6-tris(3,5-di-t-butyl-4-hydroxybenzyl) benzene, butyl hydroxy toluene, octadecyl 3.5 di-t-butyl-4-hydroxyhydrocinnamate, 4,4 methylenebis (2,6-di-butylphenol), p,p'-dioctyl diphenylamine, and 1,1, 3-tris-(2-methyl-4-hydroxy-5-t-butylphenyl) butane. When used, antioxidants are preferably present in amounts from 0.01 to 1 percent, by weight, based upon 100% total weight of coating composition.

Conventional pigments may be added to the coating mixture to impart color or radiopacity, or to improve the appearance of the coatings.

Air release agents or defoamers which are optionally included in the coating solution include, but are not limited to, polydimethyl siloxanes, 2,4,7,9-tetramethyl-5-decyn-4, 7-diol, 2-ethylhexyl alcohol, and n-beta-aminoethyl-gamma-amino-propyl-trimethoxysilane. Air release agents are preferably added in amounts from 0.005 to 0.5 percent, by weight, based upon 100% total weight of coating composition.

The following non-limiting examples are meant to be illustrative embodiments of the present invention. In each of the examples, the molecular weight of the hyaluronic acid which formed the sodium salt was approximately 720,000 daltons.

EXAMPLE 1

A diluted solution of hexamethylene diisocyanate was prepared by combining and mixing thoroughly 50.18 g. hexamethylene diisocyanate in N-methyl-2-pyrrolidone, available as Bayhydur™ BL116 from Bayer Corporation, and 46.25 g. distilled water.

The coating solution was prepared by combining, in order, the following ingredients and mixing them thoroughly:
  (a) 0.19 g. of the diluted hexamethylene diisocyanate solution;
  (b) 0.2 g. of sodium hyaluronate available from Life Core Medical; and
  (c) 20.29 g. distilled water.

The coating solution was applied to coupons A, B, and C. Coupons A, B, and C were made of stainless steel 316. Prior to coating, each coupon was washed with hexane for 15 minutes in an ultrasonic bath, rinsed with distilled water, washed with isopropyl alcohol for 15 minutes in an ultrasonic bath, rinsed with distilled water, washed with sodium hydroxide for 15 minutes, and rinsed with distilled water.

The coupons were coated by dipping them into the coating solution. The coupons were lowered into the coating solution at a speed of 110 in/min and held in the coating solution for 2 minutes. Coupons A, B, and C were withdrawn from the coating solution at speeds of 110, 42, and 10 in/min, respectively. The greater the withdrawal speed, the thicker the coating on the coupon. The coupons were then placed in an oven at 140° C. for 20 minutes to effect curing of the coating. The coating contained 1% sodium hyaluronate and 0.5% hexamethylene diisocyanate.

A toluidine blue solution was prepared by mixing 0.5 g. of toluidine blue and 98 g. of water. Each coupon was dipped into the toluidine blue solution for 30 seconds to 1 minute. Then the coupon was rubbed with finger pressure 10 to 20 times.

The rubbed coupon was again dipped in the toluidine blue solution and then observed for cracks and missing spots in the coating. A uniform coating causes the toluidine blue to adhere to the coating. In spots where the coating has been rubbed off, the toluidine blue does not adhere to the coupon. A "good stain" refers to a uniform coating after rubbing.

The lubricity of a coating was determined by comparing it to an uncoated coupon and a coupon coated with Bayhydur™ but without hyaluronic acid.

Coupon A, B, and C exhibited good stain and good slip. Excess toluidine blue easily came off coupons B and C.

Similar results are obtained when hyaluronic acid is employed in place of the sodium salt.

EXAMPLE 2

A coating solution was prepared by combining in order the following ingredients and mixing them thoroughly:
  (a) 19.2 g. distilled water;
  (b) 0.2 g. of sodium hyaluronate available from Life Core Medical; and
  (c) 0.2 g. of the diluted hexamethylene diisocyanate solution described in Example 1.

Coated coupons D, E, and F were prepared with this coating solution and tested as described in Example 1. The coating contained 1% sodium hyaluronate and 0.5% hexamethylene diisocyanate.

Coupon D exhibited dark stain and good slip. Coupons E and F exhibited good stain and good slip. Excess toluidine blue easily came off coupons D, E, and F.

Similar results are obtained when the potassium salt of hyaluronic acid is employed in place of the sodium salt.

EXAMPLE 3

A coating solution was prepared by combining in order the it following ingredients and mixing them thoroughly:
  (a) 0.42 g. of the diluted hexamethylene diisocyanate solution described in Example 1;
  (b) 0.04 g. of sodium hyaluronate available from Life Core Medical; and
  (c) 19.98 g. distilled water.

Coupons G, H, and I were prepared with this coating solution and tested as described in Example 1. The coating contained 0.2% sodium hyaluronate and 1.1% hexamethylene diisocyanate.

Coupon G exhibited good stain but was not slippery. Coupons H and I exhibited fair stain but were not slippery since the ratio of sodium hyaluronate to hexamethylene diisocyanate was 2:11, which is too low.

EXAMPLE 4

A diluted solution of sodium hyaluronate was prepared by combining and mixing thoroughly 0.2 g. sodium hyaluronate available from Life Core Medical and 99.8 g. distilled water.

A diluted solution of hexamethylene diisocyanate was prepared by combining and mixing thoroughly 10 g. hexamethylene in diisocyanate in N-methyl-2-pyrrolidone, available as Bayhydur™ BL116 from Bayer Corporation, and 10 g. tetrahydrofuran.

The coating solution was prepared by combining the following ingredients and mixing them thoroughly:

(a) 20 g. of the diluted sodium hyaluronate solution;
(b) 0.1 g. of the diluted hexamethylene diisocyanate solution; and
(c) 10 g. tetrahydrofuran.

Coupons J, K, and L were coated by dipping them into the coating solution. The coupons were lowered into the coating at a speed of 110 in/min and held in the coating solution for 2 minutes. The coupons were withdrawn from the coating solution at a speed of 42 in/min. The coating contains 0.13% sodium hyaluronate and 0.17% hexamethylene diisocyanate.

Coupons J, K, and L exhibited good stain and slight slip due to the low concentration of sodium hyaluronate in the coating.

EXAMPLE 5

A coating solution was prepared by combining the following ingredients and mixing them thoroughly:
(a) 20 g. of the diluted sodium hyaluronate solution described in Example 4;
(b) 0.2 g. of the diluted hexamethylene diisocyanate solution described in Example 4; and
(c) 10 g. tetrahydrofuran.

Coupons M, N. and O were prepared with this coating a solution and tested as described in Example 4. The coating contains 0.13% sodium hyaluronate and 0.33% hexamethylene diisocyanate.

Coupons M, N, and O exhibited good stain and slight slip due to the low concentration of sodium hyaluronate in the coating.

EXAMPLE 6

A diluted solution of hexamethylene diisocyanate was prepared by combining and mixing thoroughly 50 g. hexamethylene diisocyanate in N-methyl-2-pyrrolidone, available as Bayhydur™ BL116 from Bayer Corporation, and 46 g. distilled water.

The coating solution was prepared by combining the following ingredients and mixing them thoroughly:
(a) 20 g. of the diluted sodium hyaluronate solution described in Example 4; and
(b) 0.2 g. of the diluted hexamethylene diisocyanate solution described in Example 4.

Coupons P and Q were prepared with this coating solution and tested as described in Example 1.

Coupons P and Q exhibited some voids in the coating and slight slip due to the low concentration of sodium hyaluronate in the coating.

EXAMPLE 7–9 and 11–17 and COMPARATIVE EXAMPLE 10

For Examples 7–9 and 11–17 and Comparative Example 10, the following solutions were prepared:

A water-tetrahydrofuran solution was prepared by combining and mixing thoroughly 106.0 g. distilled water and 100.34 g. tetrahydrofuran.

A 1% sodium hyaluronate solution was prepared by combining and mixing thoroughly 1 g. sodium hyaluronate available from Life Core Medical, 49 g. distilled water and 50 g. tetrahydrofuran.

A 0.5% sodium hyaluronate solution was prepared by combining and mixing thoroughly 39.99 g. of the 1% sodium hyaluronate solution and 40.09 g. of the water-tetrahydrofuran solution.

A 0.25% sodium hyaluronate solution was prepared by combining and mixing thoroughly 0.120 g. sodium hyaluronate available from Life Core Medical and 49.10 g. distilled water.

A diluted solution of hexamethylene diisocyanate was prepared by combining and mixing thoroughly 5.03 g. hexamethylene diisocyanate in N-methyl-2-pyrrolidone, available as Bayhydur™ BL116 from Bayer Corporation, and 5.06 g. of the water-tetrahydrofuran solution.

EXAMPLE 7

A coating solution was prepared by combining the following ingredients and mixing them thoroughly:
(a) 20.01 g. of the 0.5% sodium hyaluronate solution; and
(b) 0.12 g. of the diluted hexamethylene diisocyanate solution.

Coupons R, S, and T were washed with hexane for 15 minutes in an ultrasonic bath, rinsed with distilled water, washed with isopropyl alcohol for 15 minutes in an ultrasonic bath, rinsed with distilled water, washed with sodium hydroxide for 15 minutes, rinsed with distilled water, and dried off.

The coupons were coated by dipping them into the coating solution. Each coupon was lowered into the coating solution at a speed of 110 in/min and held in the coating solution for 2 minutes. Each coupon was withdrawn from the coating solution at a speed of 42 in/min. and was air dried for 20 minutes and then placed in an oven at 140° C. for 20 minutes to effect curing of the coating.

A toluidine blue solution was prepared by mixing 0.5 g. of toluidine blue and 98 g. of water.

Coupon R was dipped in-the toluidine blue solution for approximately 1 minute and was then rubbed with finger pressure 10 to 20 times. The rubbed coupon was dipped in the toluidine blue solution and then observed for cracks and missing spots in the coating. A uniform coating causes the toluidine blue to adhere to the coating. Coupon S was also rub tested but without the toluidine blue solution. After 3 days in a flusher, coupon T was rub tested, followed by staining with toluidine blue solution to determine the durability of the coating. The flusher was a system having a continuous flow of saline at 37° C.

The lubricity of the coating was determined by comparing it to an uncoated coupon and a coupon coated with Bayhydur™, but without hyaluronic acid.

Coupon R exhibited a thick coating and good stain, but was not slippery. Coupon S was slippery. Coupon T was slippery and exhibited good stain indicating a durable coating.

EXAMPLE 8

A coating solution was prepared by combining the following ingredients and mixing them thoroughly:
(a) 19.58 g. of the 0.5% sodium hyaluronate solution; and
(b) 0.20 g. of the diluted hexamethylene diisocyanate solution.

Three coupons were prepared with this coating solution and tested as described in Example 7. A fourth coupon was prepared with this coating solution and rub tested with the toluidine blue solution after 8 days in a flusher to determine the durability of the coating. The fourth coupon was also tested for lubricity as described in Example 7.

The first coupon exhibited a thick coating and good stain but was not slippery; the second coupon was slippery; the third coupon exhibited a durable coating and was very slippery after three days in a flusher; and the fourth coupon also exhibited a durable coating and was slippery after eight days in a flusher.

EXAMPLE 9

A coating solution was prepared by combining the following ingredients and mixing them thoroughly:

(a) 19.98 g. of the 0.5% sodium hyaluronate solution; and (b) 0.41 g. of the diluted hexamethylene diisocyanate solution.

Three coupons were prepared with this coating solution and tested as described in Example 7.

The first coupon exhibited a thick coating and good stain, but was not slippery; the second coupon was slippery; and the third coupon exhibited a durable coating and was very slippery after three days in a flusher.

COMPARATIVE EXAMPLE 10

The coating solution was prepared by combining the following ingredients and mixing them thoroughly:

(a) 15.03 g. of hexamethylene diisocyanate in N-methyl-2-pyrrolidone available as Bayhydur™ BL116 from Bayer Corporation; and (b) 15.07 g. of the tetrahydrofuran-water solution.

Two coupons were prepared with this coating solution and tested as described in Example 7. The second coupon was tested without the toluidine blue solution.

The first coupon exhibited no stain and was not slippery. The second coupon was not slippery.

EXAMPLE 11

A coating solution was prepared by combining the following ingredients and mixing them thoroughly:

(a) 10.00 g. of the coating solution of Example 7; and (b) 10.03 g. of the water-tetrahydrofuran solution.

A coupon prepared with this coating solution and tested in a flusher for 3 days as described in Example 7 exhibited good stain and was slippery.

EXAMPLE 12

A coating solution was prepared by combining the following ingredients and mixing them thoroughly:

(a) 10.01 g. of the coating solution of Example 8; and (b) 10.02 g. of the water-tetrahydrofuran solution.

A coupon prepared with this coating solution and tested in a flusher for 3 days as described in Example 7 exhibited good stain and was slippery.

EXAMPLE 13

A coating solution was prepared by combining the following ingredients and mixing them thoroughly:

(a) 10.07 g. of the coating solution of Example 9; and (b) 10.04 g. of the water-tetrahydrofuran solution.

A coupon prepared with this coating solution and tested in a flusher for 3 days as described in Example 7 exhibited good stain and was slippery.

EXAMPLE 14

A coating solution was prepared by combining the following ingredients and mixing them thoroughly:

(a) 20.08 g. of the 0.25% sodium hyaluronate solution; and (b) 0.05 g. of the diluted hexamethylene diisocyanate solution.

A coupon prepared with this coating solution was tested for lubricity and durability, as described in Example 7; it exhibited good stain and was slippery. The coating contained 0.25% sodium hyaluronate.

EXAMPLE 15

A coating solution was prepared by combining the following ingredients and mixing them thoroughly:

(a) 19.98 g. of the 0.25% sodium hyaluronate solution; and (b) 0.1 g. of the diluted hexamethylene diisocyanate solution.

A coupon prepared with this coating solution was tested for lubricity and durability, as described in Example 7; it exhibited good stain and was slippery. The coating contained 0.25% sodium hyaluronate.

EXAMPLE 16

A coating solution was prepared by combining the following ingredients and mixing them thoroughly:

(a) 10 g. of the coating solution of Example 14; and (b) 10 g. of the tetrahydrofuran-water solution.

A coupon prepared with this coating solution, rub tested, and tested for lubricity as described in Example 7 exhibited good stain and was only slightly slippery. The coating contained 0.125% sodium hyaluronate.

EXAMPLE 17

A coating solution was prepared by combining the following ingredients and mixing them thoroughly:

(a) 10 g. of the coating solution of Example 15; and (b) 10 g. of the tetrahydrofuran-water solution.

A coupon prepared with this coating solution, rub tested, and tested for lubricity as described in Example 7 exhibited good stain and was only slightly slippery. The coating contained 0.125% sodium hyaluronate.

While a preferred embodiment of the present invention has been described, it should be understood that various changes, adaptations and modifications may be made therein without departing from the spirit of the invention and the scope of the appended claims.

What is claimed is:

1. A method of preparing a coating on a substrate comprising:

forming a mixture of hyaluronic acid or a salt thereof and a blocked polyisocyanate in a solvent comprising water;

applying said mixture to said substrate; and curing said mixture on said substrate to form said coating.

2. The method of preparing a coating on a substrate according to claim 1, wherein said curing comprises:

(a) air drying said coating after application; and (b) heating said coating mixture at from about 120 to about 180° C.

3. The method of preparing a coating on a substrate according to claim 1, wherein said forming comprises:

(a) mixing said hyaluronic acid and said solvent to yield a hyaluronic acid solution;

(b) mixing said blocked polyisocyanate and said solvent to yield a blocked polyisocyanate solution; and (c) mixing said hyaluronic acid solution and said blocked polyisocyanate solution.

4. A coated substrate made by the method of claim 1.

* * * * *